(12) United States Patent
Fernandes et al.

(10) Patent No.: US 8,445,452 B2
(45) Date of Patent: May 21, 2013

(54) FULVIC ACID AND ANTIBIOTIC COMBINATION

(75) Inventors: Antonio Celestino Fernandes, Pretoria (ZA); Constance Elizabeth Medlen, Pretoria (ZA); Stephen Leivers, Cape Town (ZA)

(73) Assignee: Pfeinsmith Ltd., Ebene (MU)

( * ) Notice: Subject to any disclaimer, the term of this patent is extended or adjusted under 35 U.S.C. 154(b) by 146 days.

(21) Appl. No.: 12/996,480

(22) PCT Filed: Jun. 4, 2009

(86) PCT No.: PCT/IB2009/052366
§ 371 (c)(1),
(2), (4) Date: Mar. 30, 2011

(87) PCT Pub. No.: WO2009/147635
PCT Pub. Date: Dec. 10, 2009

(65) Prior Publication Data
US 2011/0207687 A1   Aug. 25, 2011

(30) Foreign Application Priority Data

Jun. 5, 2008   (ZA) .............................. 2008/04901

(51) Int. Cl.
*A61K 31/70* (2006.01)
*A61K 31/35* (2006.01)
*A61K 31/215* (2006.01)

(52) U.S. Cl.
USPC .............................. 514/40; 514/456; 514/530

(58) Field of Classification Search
USPC ................... 514/35, 36, 37, 38, 40, 456, 530
See application file for complete search history.

(56) References Cited

U.S. PATENT DOCUMENTS 5,204,368 A    4/1993  Cronje et al.

FOREIGN PATENT DOCUMENTS

| | | |
|---|---|---|
| CN | 1276360 A | 12/2000 |
| EP | 1 698 333 A1 | 9/2006 |
| EP | 1698333 A1 | 9/2006 |
| EP | 2 062 582 A1 | 5/2009 |
| EP | 2062582 A1 | 5/2009 |
| WO | 2007125492 A2 | 11/2007 |
| WO | WO 2007125492 A2 | 11/2007 |
| WO | WO 2007125492 A3 | 11/2007 |

OTHER PUBLICATIONS

First Office Action, China Patent Office, Dec. 7, 2011 in Chinese Application 200980128246.4.

*Primary Examiner* — Elli Peselev

(57) ABSTRACT

This invention relates to a fulvic acid and antibiotic combination for use in the treatment of various diseases and conditions. The invention further relates to the use of the combination for the treatment of various diseases and conditions, including bacterial infection. In particular, the bacteria are antibiotic resistant bacteria.

8 Claims, 4 Drawing Sheets

FULVIC ACID AND ANTIBIOTIC COMBINATION

BACKGROUND OF THE INVENTION

THIS invention relates to a combination of fulvic acid and one or more antibiotics from the classes of penicillins and aminoglycosides for use in the treatment of various conditions.

Humic substances are formed during the decay of plant and animal residues in the environment (MacCarthy et al., 1985). These substances can be divided into humic acid, fulvic acid and humin on the basis of the solubility in water as a function of pH. Fulvic acid is the fraction that is soluble in water under all pH conditions and is in general lower in molecular size and weight and lower in colour intensity than humic acids.

Fulvic acid occurs at low levels in soil and water in nature and is difficult to isolate. Most research on the medicinal application of fulvic acid up to date has been done on a fulvic acid product derived from bituminous coal by a controlled wet oxidation process (Bergh et al., 1997). A particularly suitable process for producing fulvic acids from coal by a wet oxidation process is described in U.S. Pat. No. 4,912,256. Fulvic acids derived from this process are often referred to as oxifulvic acids.

International patent Publication WO00/19999 discloses the use of fulvic acid in the treatment of inflammation, acne, eczema, and bacterial, fungal and viral infections.

U.S. Pat. Nos. 4,999,202 and 5,204,368 disclose compositions containing fulvic acid, salt or a derivative thereof, which have bacteriostatic or bacteriocidal properties and are useful as disinfectants.

Fulvic acids derived from oxidation of coal contain high concentrations of heavy metals including aluminium, mercury, cadmium, chromium and lead that are harmful to humans and should be avoided in pharmaceutical preparations. International patent Publication WO2007/125492 discloses a fulvic acid composition derived from a carbohydrate source by wet oxidation containing a low content of these harmful elements and a method of producing such a composition. Such a composition is described as being useful for pharmaceutical application.

SUMMARY OF THE INVENTION

According to one aspect of the invention, there is provided a combination comprising fulvic acid, a salt, ester or derivative thereof and one or more antibiotics from the classes of penicillins and aminoglycosides.

Preferably, the antibiotic is selected from the group consisting of oxacillin and gentamicin, or a combination thereof.

The fulvic acid, salt, ester or derivative thereof may have any pH, from acid to basic, typically the pH is from acidic to neutral. The fulvic acid may be in the form of a solution buffered to a suitable pH. Preferably, the fulvic acid is either in the form of the acid or as a salt, e.g. potassium salt.

The preferred fulvic acid is a carbohydrate derived fulvic acid such as that described in WO2007/125492. The fulvic acid described in this publication is has a molecular weight not exceeding 20,000 Daltons, and a low content of the elements aluminium, mercury, cadmium, chromium and lead. Preferably the content of these elements does not exceed 20 ppm. The fulvic acid is derived from a carbohydrate such as a saccharide. The preferred saccharide is sucrose, glucose or fructose.

The combination may be formulated into a pharmaceutical dosage form, more particularly a liquid, tablet, capsule, cream, gel or the like.

According to another aspect of the invention is provided a combination according to the invention for use in a method of treatment or inhibition of a disease or condition in a subject, the method comprising administration of the combination to the subject.

According to a further aspect of the invention is provided the use of the combination of the invention in the manufacture of a pharmaceutical composition for use in a method of treatment or inhibition of a disease or condition in a subject, the method comprising administration of the combination to the subject.

According to a further aspect of the invention is provided a combination according to the invention for use in a method of killing, inhibiting or preventing bacterial growth.

According to a further aspect of the invention is provided a method of killing, inhibiting or preventing bacterial growth by the use of the combination of the invention.

According to a further aspect of the invention is provided a method of treating, inhibiting or preventing a disease or condition in a subject by administration of an effective amount of the combination of the invention.

The disease or condition may be a bacterial infection, preferably the bacteria are antibiotic resistant bacteria, more particularly the bacteria are multiple drug resistant bacteria, such as MRSA (multiple drug resistant *Staphylococcus aureus*).

The bacteria may be resistant to one or more antibiotics from the classes of penicillins and aminoglycosides. Preferably, the antibiotics are selected from the group consisting of oxacillin and gentamicin, and a combination thereof.

The administration may be oral, topical or any other suitable form of administration.

The subject may be an animal or a human.

The use or administration of the combination of the invention may be more effective than the use or administration of the fulvic acid, salt, ester or derivative thereof or the antibiotic alone.

In one form of the invention, it has been found that the bacteria may not develop resistance to the combination of fulvic acid, a salt, ester or derivative thereof and oxacillin for up to about 5 days of exposure to the combination, more preferably for up to about 10 days of exposure to the combination, even more preferably for up to about 20 days of exposure to the combination.

The use of fulvic acid, salt, ester or derivative thereof has been found to enhance the antibiotic properties of two classes of antibiotic, particularly oxacillin and gentamicin, or any combination thereof.

DESCRIPTION OF PREFERRED EMBODIMENTS

Drug resistance, in particular multiple drug resistance (MRA) has become a major problem in the treatment of various diseases and conditions, in particular those caused by bacterial agents. A treatment strategy that is effective against these resistant strains is therefore needed.

Two studies were conducted to evaluate the antibacterial characteristics of fulvic acid alone or together with antibiotics from the classes of penicillins and aminoglycosides against specific organisms, in particular bacteria, more particularly certain antibiotic resistant bacteria. The fulvic acid was that described in, and produced by the method described in WO 2007/125492 and is hereinafter referred to as CHD-FA.

In the first study, the antibacterial efficacy of fulvic acid alone or together with oxacillin or gentamicin was assessed.

The second study assessed the development of bacterial resistance to fulvic acid with or without antibiotic over time.

The following examples are for the purpose of illustration only and are not to be construed as limiting on the invention in any way.

EXAMPLE 1

Antibacterial Characteristics of Fulvic Acid

Figure 1:
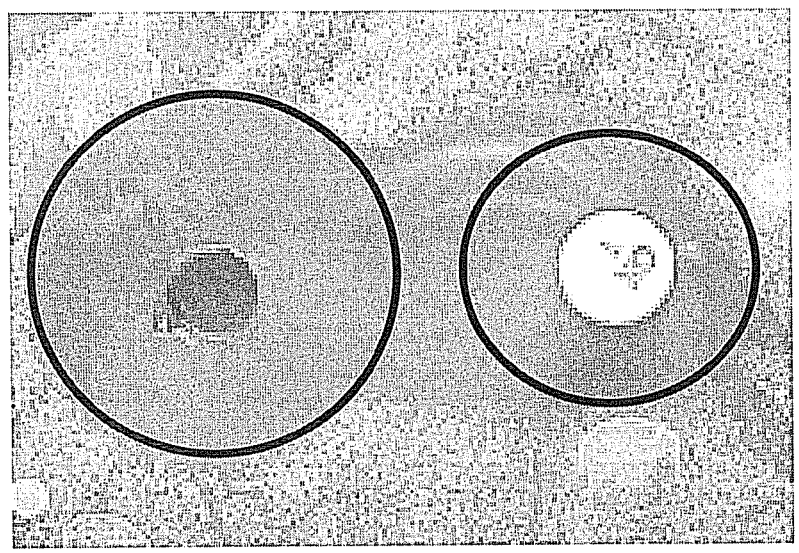
FIG. 1 Shows the synergy between fulvic acid and oxacillin, on a lawn of *S. aureus* ATCC 12600.
Figure 2:
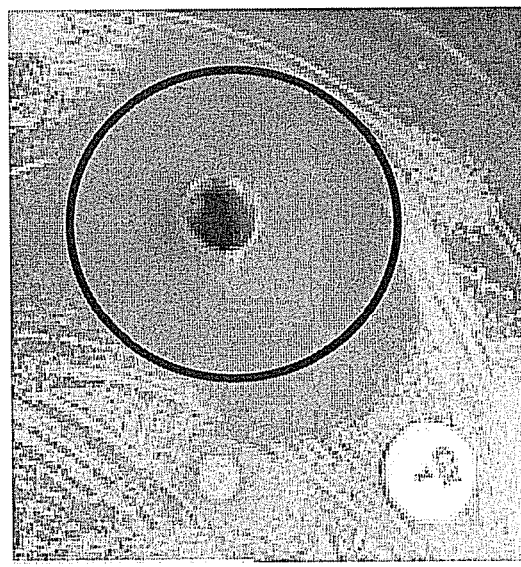
FIG. 2 Shows the synergy between fulvic acid and oxacillin, on a lawn of methicillin resistant *Staphylococcus aureus* P39380.
Figure 3:
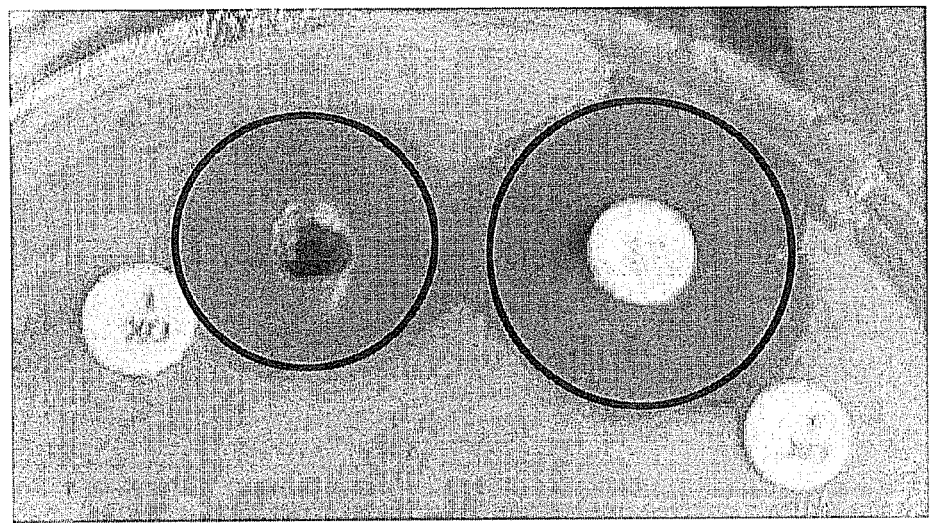
FIG. 3 Shows the synergy between fulvic acid and gentamicin, on a lawn of *P. aeruginosa* ATCC 9027.
Figure 4:
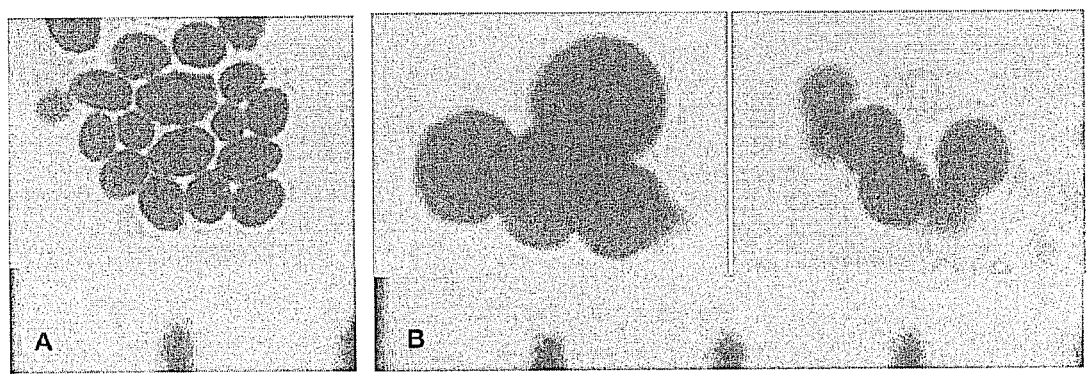
FIG. 4 Shows a Gram stain of *C. albicans* not subjected to fulvic acid (a) and harvested from within the zone of inhibition due to fulvic acid (b).

A study was conducted to determine the antibacterial characteristics of fulvic acid. Radial zones of inhibition of microbial growth and broth serial dilution methods were used to determine the antimicrobial activity of this product. Results showed that fulvic acid has antimicrobial activity against *Enterococcus faecalis* (ATCC 51575), *Salmonella enterica* (ATCC 700565) *Staphylococus aureus* (ATCC 12600), multidrug-resistant *Staphylococcus aureus* (MRSA) (ATCC) (P3938), *Escherichia coli* (ATCC 1173) and *Pseudomonas aeruginosa* (ATCC 6027). The antimicrobial spectrum of CHD-FA was shown to act synergistically with gentamicin and oxacillin (methicillin) (FIGS. 1 to 3). A Gram stain of *C. albicans* grown in the presence of fulvic acid showed rounded enlarged non-dividing bodies indicating that this product acts on the cell wall of microorganisms (FIG. 4).

Methods
Specimen Tested

The specimen used was carbohydrate derived fulvic acid (CHD-FA). The CHD-FA was a brown liquid containing 3.5% fulvic acid at a pH of 2.14. The fulvic acid had a content of the elements aluminium, mercury, cadmium, chromium and lead which was below 20 ppm and was produced by the method described in WO2007/125492.

Microbial Strains Used

The following strains were used:

*Escherichia coli* (ATCC 1173), *P. aeruginosa* (ATCC 6027), *S. aureus* (ATCC 12600), a recently isolated *S. aureus* that was coagulase negative, *Staphylococcus epidermidis* (recent isolate) and *E. coli* (ATCC1173). *S. aureus* strains that were used for comparative studies with presently prescribed antibiotics were recent clinical isolates labeled 22225 (resistant to erythromycin) and two methicillin resistant *S. aureus* (MRSA) strains 2606 (resistant to ampicillin, oxacillin (methicillin) and slightly sensitive to gentamicin) and P3938 (MRSA strain; resistant to erythromycin, oxacillin (methicillin), clindamycin and slightly sensitive to fucidic acid). Two *C. albicans* strains (ATCC 10231 and ATCC 9027) and five different recently isolated *C. albicans* strains, which we labeled 42, 43, 44, UI and U7 were also tested.

Antimicrobial Activity Determined by the Radial Diffusion Inhibition Method

Radial zone inhibition of growth of microbes by CHD-FA was determined by the basic Kirby-Bauer method. In short, for quantitative analysis 50 μL of neat CHD-FA was inserted into 4.5 mm diameter wells in 4 mm deep Mueller Hinton agar (Mast Group Ltd, Merseyside, UK) on which a lawn of the relevant microbe was seeded and then incubated for 16 hours at 37° C. The lawn was established by seeding the surface of the agar plate with 50 μL of a standardized microbial suspension in saline. This suspension was obtained at a reading of 0.07 on a colorimeter (Sherwood, 254) containing a 520 optical density filter, resulting in $35 \times 10^6$ colony forming units per ml. Inhibition zone size was measured twice at right angles to each other and the average recorded.

Antibiotics were applied to the agar plates with antibiotic impregnated discs (Mast Group Ltd, Merseyside, UK) as used in routine laboratory antibiogram determinations.

Antimicrobial Activity Determined by the Serial Broth Dilution Method

The minimum lethal concentration (MLC) of CHD-FA for the different organisms was determined by two-fold serial dilutions of 0.5 ml of CHD-FA in saline followed by the addition of 0.5 ml of double strength Mueller Hinton broth (Mast Group Ltd, Merseyside, UK). The broths were inoculated with 25 μL of the standardized microbial suspension as previously described and incubated for 16 hours. The end point was assessed as the dilution of the last tube whose contents, when spotted onto Mueller Hinton agar and incubated for 16 hours, showed no growth. Appropriate positive and negative controls were included.

Synergistic Evaluation

Wells containing CHD-FA and antibiotic disks were placed at varying distances from each other on a Mueller Hinton agar plate on which a relevant microbe had been seeded as previously described; the inhibition patterns were compared to those described by Lorian (1991).

All the above investigations were conducted in triplicate and the results were averaged.

Morphological Studies of *C. albicans*

Photomicrographs were taken using a Reichert Jung microscope with a digital camera (Motic Images Plus Version 2.0 ML) connected to the microscope eyepiece. The pictures were subjected to identical conditions related to microscopy and software manipulation.

Results
Synergistic Activity of CHD-FA with Various Microbes

Synergistic activity between the carbohydrate derived fulvic acid and oxacillin (methicillin) on a lawn of *S. aureus* (ATCC 12600) is shown in FIG. 1. FIG. 2 shows synergistic activity between CHD-FA and oxacillin (methicillin) on a lawn of an MRSA strain (P3938) and FIG. 3 shows synergistic activity between fulvic acid and gentamicin on a lawn of *P. aeruginosa* (ATCC 9027).

Morphological Effect of CHD-FA on *C. albicans*.

FIG. 4b shows a Gram stain of *C. albicans* harvested from within the zone of inhibition due to CHD-FA, which can be compared with FIG. 4a a Gram stain of *C. albicans* that has not been subjected to the antimicrobial action of the CHD-FA.

Discussion

The results obtained by both the radial diffusion inhibition and the serial doubling dilution broth methods show that CHD-FA is a broad band antimicrobial, encompassing Gram positive cocci, Gram negative bacilli and yeasts. This inhibition spectrum is not seen with the present conventional prescribed antibiotics. CHD-FA was also found to be effective against the three strains of recently isolated *S. aureus*, two of which are MRSAs'. The three recently isolated *S. aureus* strains are accumulatively resistant to erythromycin, ampicillin, oxacillin (methicillin), clindamycin, gentamicin and slightly sensitive to CHD-FA.

Fulvic acid acts synergistically with oxacillin (methicillin) and gentamicin, thereby increasing its antimicrobial effectiveness, possibly by allowing better penetration of the antibiotic into the microbe by non-specific weakening action on the microbial cell walls, as illustrated in FIG. 4.

EXAMPLE 2

Development of Resistance to CHD-FA

Physical Properties of CHD-FA Also Known as Fulvic Acid

CHD-FA of Example 2 was reconstituted as a 4% solution. The solutions were stored at room temperature in the dark. All experiments in this report were completed using the third bottle which was received December 2008 directly from South Africa.

The 4% CHD-FA solution was a yellow/brown slightly viscous solution with a strong odour and a pH of 1.9 at 25° C. In this study, the CHD-FA was adjusted using 10M sodium hydroxide to give a stock solution of 4% CHD-FA with a buffered pH of 3, 5 or 7.

Methods
Bacterial Isolates

Susceptibility tests were performed on the bacterial isolate, Methicillin Resistant *Staphylococcus aureus*, EMRSA16. The EMRSA16 strain was recovered from long term storage on beads at −80° C. and grown on Mueller Hinton agar (Oxoid) at 37° C. for 24 hours.

Media

All experiments were performed using broth or agar formulations of Mueller Hinton medium (Oxoid) reconstituted as per the manufacturer's instructions.

Preparation of the Inoculum a) The EMRSA16 strain was cultured in ambient air at 37° C. on Mueller Hinton agar for 24 hours before testing.
b) The inoculum for each strain was prepared by picking distinct colonies from the culture plates and suspending them in 2 ml of Mueller Hinton broth. The turbidity was then adjusted to McFarland standard 0.5.
c) The inoculum was completely resuspended by vigorous shaking on a vortex mixer for 15 s.
d) The inocula were then adjusted by diluting 1:100 in Mueller Hinton broth for MIC testing.

Assay Conditions

Sterile plastic, disposable, microtitration plates with 96 flat-bottom wells were used.

Step 1 Addition of CHD-FA

The stock solution of CHD-FA contains 4% of the native compound. For each strain tested, 100 µL of media was added to each well 2-12. 200 µL of 4% CHD-FA was then added to wells in column 1. 100 µL amounts were then taken from wells in column 1 and diluted two fold by transferring them to column 2 with a multichannel pipette (±2% coefficient of variation). 100 µL samples were then removed from wells in column 2 and transferred to column 3, and so on through to column 10. The last 100 µL of drug is discarded. Column 11 is a positive control containing no CHD-FA and column 12 is a negative control containing diluent only.

Step 2 Addition of Oxacillin

A 1600 mg/L stock solution of oxacillin was prepared by adding 5 ml of sterile distilled water to 8 mg of oxacillin. A 1:100 dilution of the stock solution was then prepared, followed by 1:2 serial dilutions to give oxacillin dilutions ranging from 16 to 0.06 mg/L. 50 µl of the diluted oxacillin was then added to the diluted CHD-FA where appropriate to give a final concentration of 4 to 0.015 mg/L of oxacillin.

Step 3 Addition of EMRSA16 Strain

Either 100 µL or 50 µL volumes of the diluted inoculum suspension in Muller Hinton broth is added to the appropriate wells for either CHD-FA or CHD-FA+oxacillin efficacy testing respectively. This produces a well containing 200 µL final volume (made up of 100 µL diluted CHD-FA or diluents and 100 µL of inoculum in the appropriate broth for the strain or broth alone).

Step 4 Incubation of the Plates

All plates were incubated at 37° C. in an air and darkened incubator for 48 hours.

Step 5 Reading of Plates

Plates were read visually with the endpoint taken as the lowest concentration of drug that inhibited growth by 50% of that of the drug free control.

Step 6 Passage Resistance

In order to determine the effect of passage resistance on the inhibitory effect of CHD-FA+/−oxacillin on EMRSA16, 100 µL of the last well of growth on the MIC (minimum inhibitory concentration) plate was inoculated on to half a Mueller Hinton agar plate and incubated at 37° C. for 24 hrs. The growth from this plate was then used as a fresh suspension for the next passage. This was repeated for 10 passages in total with the efficacy of CHD-FA+/−oxacillin against EMRSA16 being determined after each passage.

Results
MICs Against CHD-FA+/−Oxacillin

MICs demonstrated that the efficacy of CHD-FA+/−oxacillin was stable for up to 10 passages. The MIC values for CHD-FA+/−oxacillin are detailed in Table 1.

TABLE 1

The MIC values for CHD-FA +/− oxacillin

| Passage Number | PH | MIC (%) CHD-FA | MIC (%) CHD-FA + oxacillin |
|---|---|---|---|
| 1 | 3 | 0.06 | 0.06 |
| 1 | 5 | 0.25 | 0.125 |
| 1 | 7 | 1.00 | 0.25 |
| 2 | 3 | 0.03 | 0.06 |
| 2 | 5 | 0.25 | 0.25 |
| 2 | 7 | 1.00 | 1.00 |
| 3 | 3 | 0.06 | 0.06 |
| 3 | 5 | 0.25 | 0.25 |
| 3 | 7 | 1.00 | 1.00 |
| 4 | 3 | 0.06 | 0.06 |
| 4 | 5 | 0.25 | 0.25 |
| 4 | 7 | 1.00 | 1.00 |
| 5 | 3 | 0.06 | 0.06 |
| 5 | 5 | 0.25 | 0.125 |
| 5 | 7 | 1.00 | 0.50 |
| 6 | 3 | 0.06 | 0.06 |
| 6 | 5 | 0.25 | 0.125 |
| 6 | 7 | 1.00 | 0.50 |
| 7 | 3 | 0.06 | 0.06 |
| 7 | 5 | 0.25 | 0.25 |
| 7 | 7 | 1.00 | 1.00 |
| 8 | 3 | 0.06 | 0.06 |
| 8 | 5 | 0.25 | 0.25 |
| 8 | 7 | 1.00 | 1.00 |
| 9 | 3 | 0.06 | 0.06 |
| 9 | 5 | 0.25 | 0.25 |

TABLE 1-continued

The MIC values for CHD-FA +/− oxacillin

| Passage Number | PH | MIC (%) CHD-FA | MIC (%) CHD-FA + oxacillin |
|---|---|---|---|
| 9 | 7 | 1.00 | 1.00 |
| 10 | 3 | 0.125 | 0.06 |
| 10 | 5 | 0.25 | 0.25 |
| 10 | 7 | 1.00 | 1.00 |

Endpoint MICs for CHD-FA at pH3.0.

Figure 5:
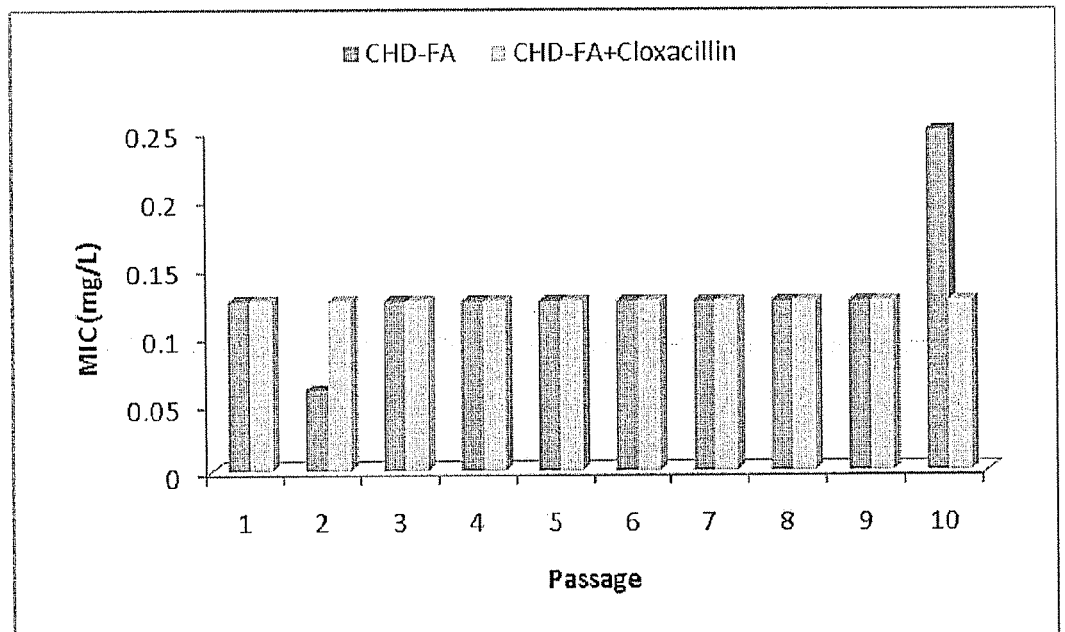
FIG. 5 Shows the endpoint MIC values for CHD-FA (pH3.0)+/−oxacillin.

The endpoint MICs demonstrated that the efficacy of CHD-FA (pH3.0)+/−oxacillin was stable for up to 10 passages, i.e. MIC outcome is no more than one well difference between each passage compared with the initial MIC measurement (passage 1) The endpoint MIC values for CHD-FA (pH3.0)+/−oxacillin are detailed in FIG. 5.

Endpoint MICs for CHD-FA at pH5.0.

Figure 6:
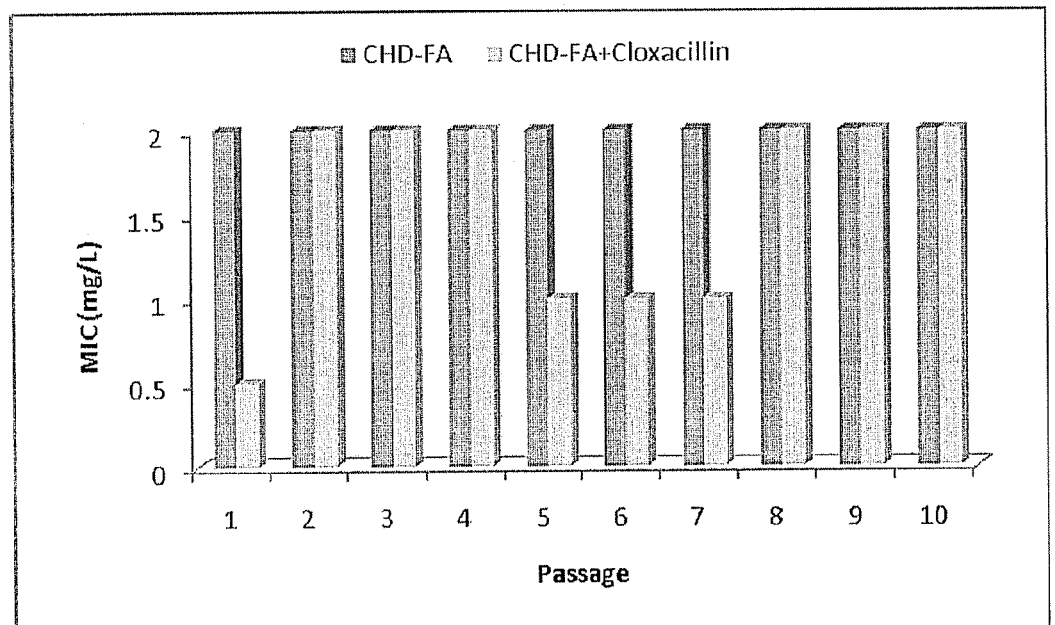
FIG. 6 Shows the endpoint MIC values for CHD-FA (pH5.0)+/−oxacillin.

The endpoint MICs demonstrated that the efficacy of CHD-FA (pH5.0)+/−oxacillin was similar for up to 10 passages, i.e. MIC outcome is no more than one well difference between each passage compared with the initial MIC measurement (passage 1) The endpoint MIC values for CHD-FA (pH5.0)+/−oxacillin are detailed in FIG. 6.

Endpoint MICs for CHD-FA at pH7.0.

Figure 7:
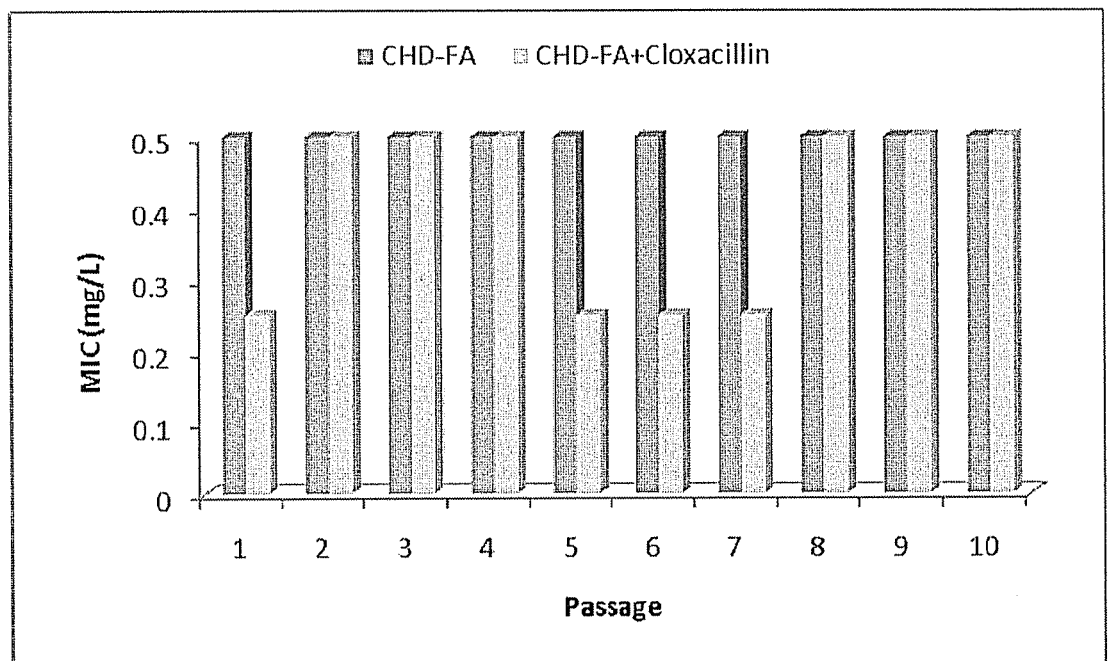
FIG. 7 Shows the endpoint MIC values for CHD-FA (pH7.0)+/−oxacillin.

The endpoint MICs demonstrated that the efficacy of CHD-FA (pH7.0)+/−oxacillin was stable for up to 10 passages, i.e. MIC outcome is no more than one well difference between each passage compared with the initial MIC measurement (passage 1) The endpoint MIC values for CHD-FA (pH7.0)+/−oxacillin are detailed in FIG. 7.

In conclusion:
- CHD-FA is effective against EMRSA16 in vitro whether examined at buffered pHs of 3.0, 5.0 or 7.0.
- CHD-FA plus oxacillin is effective against EMRSA16 in vitro whether examined at buffered pHs of 3.0, 5.0 or 7.0.
- Sequential passages of EMRSA16 in the presence of just sub-inhibitory levels of CHD-FA had no effect on the MIC.
- Sequential passages of EMRSA16 in the presence of just sub-inhibitory levels of CHD-FA plus oxacillin had no effect on the combination MIC.
- The MIC of CHD-FA against EMRSA16 was stable following >20 days exposure to the compound in serial passage.
- There was no development of resistance observed with CHD-FA monotherapy or CHD-FA in combination with oxacillin against MRSA16.

REFERENCES

Bergh J. J., Cronje I. J., Dekker J., Dekker T. G., Gerritsma L. M. & Mienie L. J. 1997. Non-catalytic oxidation of water-slurried coal with oxygen: identification of fulvic acids and acute toxicity. Fuel 76, 149-154 (1997).

Lorian, V. Antibiotics in Laboratory Medicine $3^{rd}$ Edition, 1991, p 44 and p 447.

MacCarthy P, Clapp C E, Malcolm R L, Bloom P R. Humic substances in soil and crop sciences: selected readings. Proceedings of a symposium by International Humic Substances Society, Soil Science Society of America, American Society of Agronomy and Crop Science Society of America, Chigaco, Ill., 2 Dec. 1985.

The invention claimed is:

1. A method of treating or, inhibiting a bacterial infection in a subject, comprising administering to a subject in need thereof an effective amount of a composition comprising a combination of:
   (a) fulvic acid, or a salt thereof; and
   (b) one or more antibiotics selected from the group consisting of oxacillin, gentamicin, and a combination thereof.

2. The method according to claim 1, wherein the bacteria are antibiotic resistant bacteria.

3. The method according to claim 2, wherein the bacteria are multiple drug resistant bacteria.

4. The method according to claim 2, wherein the bacteria are resistant to oxacillin, gentamicin, or both oxacillin and gentamicin.

5. The method according to claim 1, wherein the administration is oral or topical.

6. The method according to claim 1, wherein the subject is an non-human animal or a human.

7. The method according to claim 2, wherein the bacteria do not develop resistance to the composition comprising the combination of:
   (i) the fulvic acid, or the salt, thereof, and
   (ii) oxacillin for up to about 20 days of exposure to the composition.

8. The method according to claim 1, wherein the fulvic acid is carbohydrate-derived.

* * * * *